United States Patent
Long

(10) Patent No.: US 9,078,432 B2
(45) Date of Patent: *Jul. 14, 2015

(54) STABLE, CONCENTRATED HERBICIDAL COMPOSITIONS

(71) Applicant: Bayer CropScience LP, Research Triangle Park, NC (US)

(72) Inventor: David A. Long, Lee's Summit, MO (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,813

(22) Filed: May 5, 2014

(65) Prior Publication Data

US 2014/0243202 A1    Aug. 28, 2014

Related U.S. Application Data

(60) Continuation of application No. 13/691,411, filed on Nov. 30, 2012, now abandoned, which is a continuation of application No. 12/910,243, filed on Oct. 22, 2010, now Pat. No. 8,445,406, which is a division of application No. 11/347,773, filed on Feb. 3, 2006, now Pat. No. 7,842,647.

(51) Int. Cl.
| | |
|---|---|
| *A01N 57/18* | (2006.01) |
| *A01N 25/22* | (2006.01) |
| *A01N 25/02* | (2006.01) |
| *A01N 25/30* | (2006.01) |
| *A01N 57/20* | (2006.01) |

(52) U.S. Cl.
CPC ............... *A01N 25/22* (2013.01); *A01N 25/02* (2013.01); *A01N 25/30* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 4,400,196 A | 8/1983 | Albrecht et al. | |
| 5,258,358 A * | 11/1993 | Kocur et al. | 504/205 |
| 6,255,253 B1 | 7/2001 | Foerster et al. | |
| 7,842,647 B2 * | 11/2010 | Long | 504/198 |
| 8,445,406 B2 * | 5/2013 | Long | 504/198 |

FOREIGN PATENT DOCUMENTS

| | | |
|---|---|---|
| AU | 42434/89 B | 8/1992 |
| EP | 0048436 A1 | 3/1982 |
| EP | 0364202 A2 | 4/1990 |
| EP | 0511611 A1 | 11/1992 |
| WO | 9412601 A1 | 6/1994 |
| WO | 0246343 A1 | 6/2002 |
| WO | 2005117583 | 12/2005 |
| WO | 2005117583 A2 | 12/2005 |
| WO | WO 2005117583 * | 12/2005 |

OTHER PUBLICATIONS

International Search Report for PCT/US2007/002963 filed Jan. 27, 2007.
STN Jun. 5, 1992, Fluowet PL 80, registry No. 141615-38-5.
TTN Nov. 16, 1984, Plantapon CMGS, registry No. 61789-04-06.

* cited by examiner

*Primary Examiner* — Alton Pryor

(57) ABSTRACT

A liquid herbicidal composition is provided, comprising:
- a. 20 to 35 percent by weight, based on the total weight of the composition, of a water-soluble herbicidal ingredient;
- b. a $C_{12}$-$C_{16}$ alkyl ether sulfate;
- c. an organic solvent; and
- d. an alkyl polyglucoside.

The composition is stable; i.e., it occurs in a substantially continuous, single phase at temperatures as low as −20° C. It also has a viscosity of no more than 2000 cps at temperatures as low as 0° C.

12 Claims, No Drawings

STABLE, CONCENTRATED HERBICIDAL COMPOSITIONS

PRIORITY

This application is a continuation of U.S. application Ser. No. 13/691,411 filed Nov. 30, 2012, which is a continuation of U.S. application Ser. No. 12/910,243, filed Oct. 22, 2010, now U.S. Pat. No. 8,445,406, which is a divisional application of U.S. application Ser. No. 11/347,773, filed Feb. 3, 2006, now U.S. Pat. No. 7,842,647, the entire contents of which are hereby incorporated by reference in its entirety.

FIELD OF THE INVENTION

The present invention is directed to biologically active crop protection formulations, in particular, herbicidal compositions.

BACKGROUND OF THE INVENTION

Aqueous herbicidal formulations of glufosinate-ammonium have been available for decades as crop protectants. Popular formulations include surfactants, which increase the biological activity of the herbicide. High concentration formulations are being sought as well for the numerous advantages they offer; for example, less packaging is needed than with low-concentration formulations, corresponding to reductions in the cost and inconveniences of production, transit, and storage. Preparation of spray liquors is also simplified by the smaller quantities of crop protectant that need to be handled. However, certain drawbacks have been observed in higher concentration formulations. For example, the biological activity of the active ingredient is dependent on the proportion of active ingredient to surfactant, but if the amount of surfactant is too high, the viscosity of the composition may become too high for easy handling or spraying. Product instability such as phase separation has also been a drawback of highly concentrated formulations. Phase separation is undesirable because the concentration of various essential ingredients is no longer uniform throughout the composition.

It would be desirable to provide a high-concentration herbicidal composition that overcomes the drawbacks of the prior art by demonstrating enhanced biological activity in a stable formulation without compromising viscosity requirements.

SUMMARY OF THE INVENTION

A liquid herbicidal composition is provided, comprising:
a. 20 to 35 percent by weight, based on the total weight of the composition, of a water-soluble herbicidal ingredient;
b. a $C_{12}$-$C_{16}$ alkyl ether sulfate;
c. an organic solvent; and
d. an alkyl polyglucoside.

The composition is stable, occurring in a substantially continuous, single phase at temperatures as low as −20° C. It also has a viscosity of no more than 2000 cps at temperatures as low as 0° C.

DETAILED DESCRIPTION OF THE INVENTION

Other than in the operating examples, or where otherwise indicated, a numbers expressing quantities of ingredients, reaction conditions and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of 1" to 10" is intended to include all sub-ranges between and including the recited minimum value of 1 and the recited maximum value of 10, that is having a minimum value equal to or greater than 1 and a maximum value of equal to or less than 10.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Rural encompasses singular and vice versa; e. g., the singular forms "a," "an" and "the" include plural referents unless expressly and unequivocally limited to one referent. Also, as used herein, the term "polymer" is meant to refer to prepolymers, oligomers and both homopolymers and copolymers; the prefix "poly" refers to two or more.

With respect to the present invention, the term "stable" as used herein is intended to refer to physically stable compositions; i. e., liquid compositions that exist in a substantially continuous, single phase.

In the context of the present invention the term "organic solvents" refers to, for example, nonpolar solvents, polar protic solvents, aprotic polar solvents and mixtures thereof.

The liquid herbicidal composition of the present invention comprises a water-soluble herbicidal ingredient (a). Non-limiting, suitable examples include glufosinate and salts thereof such as glufosinate-ammonium, glyphosate and salts thereof, paraquat, diquat, and the like. Mixtures may also be used.

Typically the water-soluble herbicidal ingredient may comprise a compound of the formula (I) and/or salts thereof:

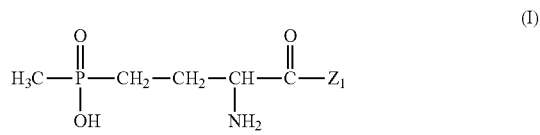

wherein $Z_1$ is a radical of the formula —OM, —NHCH($CH_3$)CONHCH($CH_3$)$CO_2$M, or —NHCH($CH_3$)CONHCH[$CH_2$CH($CH_3$)$_2$]$CO_2$M, where M is H or a salt-forming cation.

The water-soluble herbicidal ingredient may alternatively or additionally comprise a compound of the formula (II) and/or salts thereat:

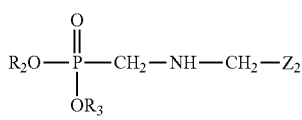

wherein $Z_2$ is a radical of the formula CN or $CO_2R_1$, in which $R_1$ is a salt-forming cation or is H, alkyl, alkenyl, alkoxyalkyl or $C_6$-$C_{10}$ aryl, which is unsubstituted or substituted, and is often unsubstituted or substituted by one or more radicals such as alkyl, alkoxy, halogen $CF_3$, $NO_2$ and CN; and wherein $R_2$ and $R_3$ are each independently H, alkyl or $C_6$-$C_{10}$ aryl, which is unsubstituted or substituted and is often unsubstituted or substituted by one or more radicals such as alkyl alkoxy, halogen, $CF_3$, $NO_2$ and CN, or biphenylyl or a salt-forming cation. Typically, the carbon-containing radicals defined as $R_2$ or $R_3$ have up to 10 carbon atoms, usually up to 6 carbon atoms.

Note that the compounds of formula (I) contain an asymmetric carbon atom. The L enantiomer has been observed to be the biologically active isomer. The formula (I) therefore is intended to encompass all stereoisomers and mixtures thereof, particularly the racemate, and the biologically active enantiomer in each case. Examples of active ingredients of the formula (I) include glufosinate and/or its ammonium salt such as in a racemic mixture: i.e., 2-amino-4[hydroxy(methyl)phosphinoyl]butanoic acid and its ammonium salt, the L enantiomer of glufosinate and its ammonium salt or other salts such as potassium, sodium, diethylamine, triethylamine, bilanafos/bialaphos; e. g., L-2-amino-4-[hydroxy(methyl)phosphinoyl]butanoyl-L-alaninyl-L-alanine and its sodium salt.

The water-soluble herbicidal ingredient may be present in the composition of the present invention in an amount of 20 to 35 percent by weight, often 20 to 30 percent by weight, and more often 22 to 28 percent by weight, based on the total weight of the composition. Note that because the water-soluble herbicidal ingredient is typically provided in a 50 percent by weight aqueous solution, an equal amount of water is usually provided with the water-soluble herbicidal ingredient. The numbers in the ranges above reflect the amount of herbicide only, not the total solution amount. Additional water may be added as necessary.

The composition of the present invention further comprises an alkyl ether sulfate (b). Alkyl ether sulfates are generally defined as salts of sulfated adducts of ethylene oxide with fatty alcohols containing from 8 to 16 carbon atoms. The alkyl ether sulfates used in the composition of the present invention are commercially available and may contain a linear aliphatic group having from 8 to 16 carbon atoms, usually from 12 to 16 carbon atoms. The degree of ethoxylation may be from 1 to 10 moles of ethylene oxide, usually 2 to 4 moles of ethylene oxide. Examples include sodium lauryl ether sulfate, ammonium lauryl ether sulfate, and other salts of lauryl ether sulfate. The alkyl ether sulfate most often used in composition of the present invention is sodium lauryl ether sulfate (SLES); typically supplied as an approximate 70% active solution, derived either from vegetable or petroleum sources.

The alkyl ether sulfate may be present in the composition of the present invention in an amount of 3 to 35 percent by weight, often 10 to 30 percent by weight, more often 20 to 30 percent by weight, based on the total weight of the composition.

The composition of the present invention further comprises an organic solvent (c). Suitable solvents may include cyclic alcohols such as tetrahydrofurfuryl alcohol; aliphatic alcohols, such as alkanols having 1 to 12 carbon atoms, usually 1 to 6 carbon atoms, such as methanol, ethanol, propanol, isopropanol and butanol, for example, or polyhydric alcohols such as ethylene glycol, propylene glycol, dipropylene glycol, and glycerol; ethers such as diethyl ether, tetrahydrofuran (THF), and dioxane; alkylene glycol monoalkyl and dialkyl ethers, such as propylene glycol monomethyl ether, propylene glycol monoethyl ether, ethylene glycol monomethyl and monoethyl ether, diglyme, and tetraglyme, for example; amides such as dimethylformamide (DMF), dimethylacetamide, dimethylcaprylamide, dimethylcapramide (HALLCOMID®), and N-alkylpyrrolidones; ketones such as acetone, cyclohexanone, acetophenone, butrylolactone; esters based on glyceryl and carboxylic acids, such as glyceryl mono-, di- and triacetate, phthalic esters, ethyl lactate, 2-ethylhexyl lactate; lactams; carbonic diesters; nitriles such as acetonitrile, propionitrile, butyronitrile, and benzonitrile; sulfoxides and sulfones such as dimethyl sulfoxide (DMSO) and sulfolane; carbonates such as propylene or butylene carbonate. Combinations of different solvents, additionally containing alcohols such as methanol, ethanol, n- and isopropanol, and n-, iso-, tert- and 2-butanol, are also suitable.

Solvents that are most often used in the composition of the present invention include individual solvents or solvent mixtures that are substantially miscible with water, in order to maintain the phase stability of the composition.

The organic solvent may be present in the composition of the present invention in an amount of 1 to 20 percent by weight, often 3 to 10 percent by weight, based on the total weight of the composition.

The alkyl polyglucosides (d) which may be used in the present invention are those corresponding to formula (III):

$$R_4O(R_5O)_b(Z_3)_a \qquad (III)$$

wherein $R_4$ is a monovalent organic radical having from 6 to 30 carbon atoms; $R_5$ is a divalent alkylene radical having from 2 to 4 carbon atoms; $Z_3$ is a glucose residue having 5 or 6 carbon atoms; b is a number ranging from 0 to 12; and a is a number ranging from 1 to 6. Non-limiting examples of commercially available alkyl polyglucosides include, for example, APG®, AGNIQUE®, or AGRIMUL® surfactants from Cognis Corporation, Cincinnati, Ohio; Atlox surfactants from Uniqema, New Castle, Del. 19720; or AG surfactants from AKZO NOBEL Surface Chemistry, LLC, such as:

1. AGNIQUE PG 8105 Surfactant—an alkyl polyglucoside in which the alkyl group contains 8 to 10 carbon atoms and having an average degree of polymerization of 1.5.
2. AGNIQUE PG 8166 Surfactant—an alkyl polyglucoside in which the alkyl group contains 8 to 16 carbon atoms and having an average degree of polymerization Of 1.6.
3. AGNIQUE PG 266 Surfactant—an alkyl polyglucoside in which the alkyl group contains 12 to 16 carbon atoms and having an average degree of polymerization of 1.6.
4. AGNIQUE PG 9116 Surfactant—an alkyl polyglucoside in which the alkyl group contains 9 to 11 carbon atoms and having an average degree of polymerization of 1.6.
5. AGNIQUE PG 264-U Surfactant—an alkyl polyglucoside in which the alkyl group contains 12 to 16 carbon atoms and having an average degree of polymerization of 1.4.
6. AGNIQUE PG 8107 Surfactant—a $C_{8-16}$ alkyl polyglucoside in which the alkyl group contains 8 to 10 carbon atoms and having an average degree of polymerization of 1.7.
7. AGNIQUE PG 266 Surfactant—a $C_{12-16}$ alkyl polyglucoside in which the alkyl group contains 12 to 16 carbon atoms and having an average degree of polymerization of 1.6.

8. AL 2575/AL 535 Surfactant—a $C_{8-11}$ alkyl polyglucoside in which the alkyl group contains 8 to 11 carbon atoms and having a HLB 12-13.
9. Akzo Nobel AG 6202, AG 6206, or AG 6210 surfactants which are 2 ethylhexyl branched C8; linear hexyl C6; and linear C8-C10 alkyl polyglucosides respectively.

The alkyl polyglucoside may typically comprise a $C_8$-$C_{16}$ alkyl polyglucoside. The alkyl polyglucosides most often used in the composition of the present invention are those of formula III wherein $R_4$ is a monovalent organic radical having from 8 to 10 carbon atoms; b is zero; and a is a number having a value from 1 to 3, typically 1.5 to 1,7, often 1.6.

The alkyl polyglucoside may be present in the composition of the present invention in an amount of 1 to 15 percent by weight, often 6 to 12 percent by weight, based on the total weight of the composition.

While the liquid herbicidal compositions of the present invention may be waterborne or solventborne, they are more often waterborne (aqueous).

In the composition of the present invention, the weight ratio of the water-soluble herbicidal ingredient (a) to the alkyl ether sulfate (b) may range from 1:0.2 to 1:5.0, often 1:0.8 to 1:1.2. In addition, the weight ratio of the water-soluble herbicidal ingredient (a) to the organic solvent (c) may range from 1:0.02 to 1:1, often 1:0.1 to 1:0.3. While not intending to be bound by theory, it has been observed that keeping the ratios of the various ingredients within these ranges enhances the biological activity of the herbicidal ingredient compared to when it is used alone, without compromising the stability of the composition. Moreover, the viscosity of the composition may be maintained within a desired range.

Unlike concentrated herbicidal compositions of the prior art, the composition of the present invention is both stable and sprayable over a wide temperature range. The viscosity of the composition is typically no more than 2000 cps, often no more than 1500 cps, more often no more than 1000 cps, at temperatures as low as 0° C. Viscosity may be measured using any technique known to those skilled in the art, for example, using a Brookfield Synchro-lectric Model LVT Viscometer. An apparent viscosity is measured by first stirring the sample with a glass rod for 10 seconds, placing the sample on the instrument, turning the instrument on, and measuring the value after 3 revolutions of the measuring dial. Typically the measurement is made using a #3 spindle rotating at 30 RPMs; however depending upon the viscosity of the sample, different spindles and differing rotational speeds can be utilized, as known by those skilled in the art.

The composition of the present invention may optionally include auxiliary agents commonly used in herbicide formulations and known to those skilled in the art. Examples include wetting agents, dispersants, emulsifiers, penetrants, preservatives, antifreezes and evaporation inhibitors such as glycerol and ethylene or propylene glycol, sorbitol, sodium lactate, fillers, carriers, colorants including pigments and/or dyes, pH modifiers (buffers, acids, and bases), salts such as calcium, magnesium, ammonium, potassium, sodium, and/or iron chlorides, fertilizers such as ammonium sulfate and ammonium nitrate, urea, and defoamers.

Suitable defoamers include all customary defoamers including silicone-based and those based upon perfluoroalkyl phosphinic and phosohonic acids, in particular silicone-based defoamers, such as silicone oils, for example.

Defoamers most commonly used are those from the group of linear polydimethylsiloxanes having an average dynamic viscosity, measured at 25° C., in the range from 1000 to 8000 mPas (mPas=millipascal-second), usually 1200 to 6000 mPas, and containing silica. Silica includes polysilicic acids, meta-silicic acid, ortho-silicic acid, silica gel, silicic acid gels, kieselguhr, precipitated $SiO_2$, and the like.

Defoamers from the group of linear polydimethylsiloxanes contain as the chemical backbone a compound of the formula HO—[Si($CH_3$)$_2$—O—]$_n$—H, in which the end groups are modified, by etherification for example, or are attached to the groups —Si($CH_3$)$_3$. Non-limiting examples of defoamers of this kind are RHODORSIL® Antifoam 416 (Rhodia) and RHODORSIL® Antifoam 481 (Rhodia). Other suitable defoamers are RHODORSIL® 1824, ANTIMUSSOL 4459-2 (Clariant), Defoamer V 4459 (Clariant), SE Vick and AS EM SE 39 (Wacker). The silicone oils can also be used in the form of emulsions.

The present invention will further be described by reference to the following examples. The examples are merely illustrative of the invention and are not intended to be limiting. Unless otherwise indicated, all parts are by weight.

EXAMPLES

The following examples (1 to 9) illustrate the preparation of various herbicidal compositions, demonstrating combinations of co-solvents and alkyl polyglucosides and their combined effects on stability. Examples 1, 3, and 7 are illustrative of the invention while Examples 2, 4-6, 8, and 9 are comparative. The ingredients were mixed together in a suitable vessel at room temperature in the order listed and were observed for phase separation at room temperature. Note that ingredients may be mixed in other sequences. For example, the herbicide may be added to the solvent package, provided the solution does not phase separate.

|  | 1 | 2 | 3 | 4 | 5 | 6 | 7 | 8 | 9 |
|---|---|---|---|---|---|---|---|---|---|
| Glufosinate 50% | 44.00 | 44.00 | 44.00 | 44.00 | 44.00 | 44.00 | 44.00 | 44.00 | 44.00 |
| SLES (sodium lauryl ether sulfate) 70% | 38.00 | 38.00 | 38.00 | 38.00 | 38.00 | 38.00 | 38.00 | 38.00 | 38.00 |
| BREAK THRU S200[1] | 1.00 | 1.00 | 1.00 | 1.00 | 1.00 | 1.00 | 1.00 | 1.00 | 1.00 |
| THFA (tetrahydrofurfuryl alcohol) | 7.00 | 7.00 | 7.00 | | | | | | |
| Propylene glycol monomethyl ether | | | | 7.00 | 7.00 | 7.00 | | | |
| Dipropylene Glycol | | | | | | | 7.00 | 7.00 | 7.00 |
| Iso-propanol | 3.00 | | | 3.00 | | | 3.00 | | |
| Iso-Butanol | | 3.00 | | | 3.00 | | | 3.00 | |
| 1-Butanol | | | 3.00 | | | 3.00 | | | 3.00 |
| AKZO 6206 Linear Hexyl polyglycoside[2] | 5.00 | | | | 5.00 | | 5.00 | | |

-continued

|  | 1 | 2 | 3 | 4 | 5 | 6 | 7 | 8 | 9 |
|---|---|---|---|---|---|---|---|---|---|
| AKZO 6202 2-ethylhexyl polyglycoside[3] |  | 5.00 |  | 5.00 |  |  |  |  | 5.00 |
| AL 2575 C8-10 Alkyl polyglycoside[4] |  |  | 5.00 |  | 5.00 | 5.00 |  |  |  |
| Sodium Xylene Sulfonate 40% aqueous | 1.75 |  |  |  | 1.75 |  |  |  | 1.75 |
| Sodium Toluene Sulfonate 40% aqueous |  |  | 1.75 | 1.75 |  |  |  | 1.75 |  |
| Ammonium Sulfate, Granular |  | 0.70 |  |  |  | 0.70 | 0.70 |  |  |
| FLUOWET PL80B[5] | 0.25 | 0.25 | 0.25 | 0.25 | 0.25 | 0.25 | 0.25 | 0.25 | 0.25 |
| Deionized Water |  | 1.05 |  |  |  | 1.05 | 1.05 |  |  |
| RESULTS: |  |  |  |  |  |  |  |  |  |
| Separation of sample | No | Yes | No | Yes | Yes | Yes | No | Yes | Yes |

[1]Ethoxylated trisiloxane available from Degussa Corporation
[2]Linear hexyl polyglucoside available from Akzo Nobel AG
[3]2 ethylhexyl branched polyglucoside available from Akzo Nobel
[4]$C_{8-11}$ alkyl polyglucoside in which the alkyl group contains 8 to 11 carbon atoms and has a HLB 12-13
[5]Defoamer available from Clariant

Examples 10 to 12

Examples 10 to 12 illustrate the effects of dipropylene glycol with various co-solvents. Example 10 is a composition of the present invention while Examples 11 and 12 are comparative.

|  | 10 | | 11 | | 12 | |
|---|---|---|---|---|---|---|
| INGREDIENT: | % | grams | % | grams | % | grams |
| Glufosinate 50% | 44.00 | 88.00 | 44.00 | 88.00 | 44.00 | 88.00 |
| SLES 70% | 38.00 | 76.00 | 38.00 | 76.00 | 38.00 | 76.00 |
| BREAK THRU S200 | 1.00 | 2.00 | 1.00 | 2.00 | 1.00 | 2.00 |
| Dipropylene Glycol | 7.00 | 14.00 | 7.00 | 14.00 | 7.00 | 14.00 |
| Iso-propanol | 3.00 | 6.00 |  |  |  |  |
| Iso-butanol |  |  | 3.00 | 6.00 |  |  |
| 1-butanol |  |  |  |  | 3.00 | 6.00 |
| AKZO 6206 Linear Hexyl polyglycoside |  |  | 5.00 | 10.00 |  |  |
| AKZO 6202 2-ethylhexl polyglycoside |  |  |  |  | 5.00 | 10.00 |
| AL 2575 C8-C10 Alkyl polyglycoside | 5.00 | 10.00 |  |  |  |  |
| Sodium Xylene Sulfonate 40% |  |  |  |  | 1.75 | 3.50 |
| Sodium Toluene Sulfonate 40% |  |  | 1.75 | 3.50 |  |  |
| PLANTAPON CMGS[1] | 1.75 | 3.50 |  |  |  |  |
| FLUOWET PL80B | 0.25 | 0.50 | 0.25 | 0.50 | 0.25 | 0.50 |
| TOTAL: | 100.00 | 200.00 | 100.00 | 200.00 | 100.00 | 200.00 |
| RESULTS: |  |  |  |  |  |  |
| Viscosity, cps - Initial Room Temperature |  | 140 |  | NT |  | NT |
| Appearance - Initial Room Temp. |  | no separation |  | separation |  | separation |

NT—Not Tested due to separation of samples in study.
[1]Surfactant available from Cognis-Care Chemicals

Example 13 (Comparative)

Each composition in the following example contained, in parts by weight:

| | |
|---|---|
| Glufosinate 50% Concentrate | 49 |
| BREAK THRU 9903 Antifoam[1] | 0.8 |
| BREAK THRU S200 Silicone Surfactant[2] | 0.6 |
| Potassium Hydroxide 50% Solution | 0.12 |

[1,2]Available from Degussa Corporation

| Example | SLES Solution % | AL 2575 % | THFA % | % Separation |
|---|---|---|---|---|
| 13a | 37.24 | 5.5 | 6.74 | 1.8 |
| 13b | 35.62 | 4.5 | 9.36 | 17.8 |
| 13c | 34 | 5.5 | 9.98 | 10.9 |
| 13d | 34 | 4.5 | 10.98 | 12.96 |
| 13e | 34 | 3.5 | 11.98 | 23.6 |
| 13f | 37.24 | 3.5 | 8.74 | 12.7 |
| 13g | 36.43 | 5 | 8.05 | 10.7 |
| 13h | 35.08 | 3.5 | 10.9 | 21.8 |
| 13i | 36.16 | 3.5 | 9.82 | 16.1 |
| 13j | 35.08 | 5.5 | 8.9 | 7.4 |

While each of the mixtures in the above set exhibited some degree of separation, the amount of separation was less as the level of THFA solvent decreased and the level of APG surfactant increased. Percent separation is a measurement of the height of a separated phase compared to the total height of a sample.

Example 14

The following example illustrates the preparation of an herbicidal composition in accordance with the present invention. The ingredients were mixed together in the order listed:

| | Percent by weight |
|---|---|
| INGREDIENT: | |
| Glufosinate 50% | 48.600 |
| AGNIQUE SLES 270[1] | 34.544 |
| AGNIQUE PG 8105[2] | 9.850 |
| THFA | 5.500 |
| BREAK THRU S200 | 0.600 |
| BREAK THRU AF 9903 | 0.800 |
| Potassium Hydroxide 50% Solution | 0.100 |
| D&C Red 17 | 0.006 |
| TOTAL | 100.000 |
| RESULTS | |
| Gms Glufosinate/liter | 280.00 |
| Lbs Glufosinate/Gal | 2.335 |
| Viscosity cps - R.T. | 216 |
| Viscosity cps - 40° F./4.4° C. | 640 |
| Viscosity cps - 32° F./0° C. | 788 |
| Viscosity cps - 12° F./–10° C. | 5400 |

[1,2]Available from AKZO NOBEL Surface Chemistry, LLC

Whereas particular embodiments of this invention have been described above for purposes of illustration, it will be evident to those skilled in the art that numerous variations of the details of the present invention may be made without departing from the invention as defined in the appended claims.

What is claimed is:

1. A liquid herbicidal composition comprising:
   a. glufosinate or a salt thereof;
   b. a lauryl ether sulfate or a salt thereof;
   c. an organic solvent selected from the group consisting of propylene glycol monomethyl ether, tetrahydrofurfuryl alcohol, dipropylene glycol, and iso-propanol; and
   d. a surfactant, wherein said surfactant comprises an alkyl polyglucoside, and
   wherein the composition is present in a continuous, single phase at a temperature as low as −20° C. and has a viscosity of no more than 2000 cps at temperatures as low as 0° C.

2. The liquid herbicidal composition of claim 1, wherein said glufosinate or salt thereof is present in an amount from 20 to 35 percent by weight, based on the total weight of the composition.

3. The liquid herbicidal composition of claim 1, wherein the organic solvent is present in an amount of 1 to 20 percent by weight, based on the total weight of the composition.

4. The liquid herbicidal composition 1, wherein said surfactant comprises an alkyl polyglucoside and is present in an amount of 1 to 15 percent by weight, based on the total weight of the composition.

5. The liquid herbicidal composition 1, wherein said the weight ratio of said glufosinate or a salt thereof (a) to the lauryl ether sulfate (b) ranges from 1:0.2 to 1:5.0.

6. The liquid herbicidal composition of claim 1, wherein said weight ratio of said glufosinate or a salt thereof(a) to the lauryl ether sulfate (b) ranges from 1:0.8 to 1:1.2.

7. The liquid herbicidal composition of claim 1, wherein said (a) comprises a glufosinate salt selected from the group consisting of glufosinate-ammonium salt, glufosinate-potassium salt, and glufosinate-sodium salt.

8. The liquid herbicidal composition of claim 1, wherein said composition further comprises an agent selected from the group consisting of an auxiliary agent, a wetting agent, a dispersant, an emulsifier, a penetrant, a preservative, an antifreeze, and an evaporation inhibitor.

9. The liquid herbicidal composition of claim 1, wherein said organic solvent comprises propylene glycol monomethyl ether.

10. The liquid herbicidal composition of claim 1, wherein said organic solvent comprises tetrahydrofurfuryl alcohol.

11. The liquid herbicidal composition of claim 1, wherein said organic solvent comprises dipropylene glycol.

12. The liquid herbicidal composition of claim 1, wherein said organic solvent comprises iso-propanol.

* * * * *